United States Patent
Hagihara

(10) Patent No.: US 11,660,075 B2
(45) Date of Patent: May 30, 2023

(54) ULTRASOUND DIAGNOSIS APPARATUS AND ULTRASOUND PROBE

(71) Applicant: Toshiba Medical Systems Corporation, Otawara (JP)

(72) Inventor: Teruki Hagihara, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 333 days.

(21) Appl. No.: 15/843,734

(22) Filed: Dec. 15, 2017

(65) Prior Publication Data

US 2018/0168553 A1 Jun. 21, 2018

(30) Foreign Application Priority Data

Dec. 16, 2016 (JP) .............................. JP2016-244060
Nov. 17, 2017 (JP) .............................. JP2017-221480

(51) Int. Cl.
*A61B 8/00* (2006.01)
*A61B 8/14* (2006.01)
*G10K 11/34* (2006.01)
*G01S 7/52* (2006.01)
*A61B 8/08* (2006.01)

(52) U.S. Cl.
CPC ............. *A61B 8/54* (2013.01); *A61B 8/14* (2013.01); *A61B 8/5207* (2013.01); *G01S 7/5202* (2013.01); *G01S 7/5208* (2013.01); *G10K 11/346* (2013.01); *A61B 8/56* (2013.01)

(58) Field of Classification Search
CPC ............ A61B 8/54; A61B 8/5207; A61B 8/14; A61B 8/56; G10K 11/346; G01S 7/5208; G01S 7/5202
See application file for complete search history.

(56) References Cited

U.S. PATENT DOCUMENTS 4,412,544 A * 11/1983 Beretsky ............. G01S 15/8977
                                                  600/443
5,865,751 A *  2/1999 Okuno ................. G10K 11/346
                                                  600/443
(Continued)

FOREIGN PATENT DOCUMENTS

| JP | 2005-152450 | 6/2005 |
|---|---|---|
| JP | 2006-217942 | 8/2006 |

(Continued)

OTHER PUBLICATIONS

Office Action dated Aug. 10, 2021 in corresponding Japanese Application No. 2017-221480.

*Primary Examiner* — Ashley K Buran
*Assistant Examiner* — Amy Shafqat
(74) *Attorney, Agent, or Firm* — Oblon, McClelland, Maier & Neustadt, L.L.P.

(57) ABSTRACT

According to one embodiment, an ultrasound diagnosis apparatus includes a transmission beam former and a transmitting circuit. The transmission beam former generates a transmission pulse. The transmitting circuit supplies an ultrasound transducer with the transmission pulse received from the transmission beam former as a drive signal. The supply of a clock necessary for the generation of the transmission pulse is stopped during a substantial reception period of echo signals from the ultrasound transducer.

13 Claims, 13 Drawing Sheets

(56) References Cited

U.S. PATENT DOCUMENTS

| | | | |
|---|---|---|---|
| 6,679,847 B1 * | 1/2004 | Robinson | G01S 7/52028 |
| | | | 600/447 |
| 7,448,998 B2 * | 11/2008 | Robinson | G01S 7/52028 |
| | | | 600/437 |
| 2003/0011285 A1 * | 1/2003 | Ossmann | G01S 7/52079 |
| | | | 310/334 |
| 2010/0090768 A1 | 4/2010 | Yamazaki | |
| 2010/0298714 A1 * | 11/2010 | Miyajima | G01S 15/8927 |
| | | | 600/459 |
| 2012/0310096 A1 * | 12/2012 | Hongou | A61B 8/5207 |
| | | | 600/447 |
| 2013/0324853 A1 | 12/2013 | Matsuda | |
| 2014/0276003 A1 * | 9/2014 | Wang | A61B 8/5253 |
| | | | 600/424 |
| 2015/0196273 A1 * | 7/2015 | Yamamoto | G01S 7/52047 |
| | | | 600/447 |
| 2016/0374645 A1 * | 12/2016 | Kim | G01S 7/5202 |
| | | | 600/447 |
| 2017/0252012 A1 * | 9/2017 | Nagai | G01S 15/8915 |

FOREIGN PATENT DOCUMENTS

| | | |
|---|---|---|
| JP | 4599208 | 12/2010 |
| JP | 5231931 | 7/2013 |
| JP | 2013-247981 | 12/2013 |
| JP | 2015-128532 | 7/2015 |

* cited by examiner

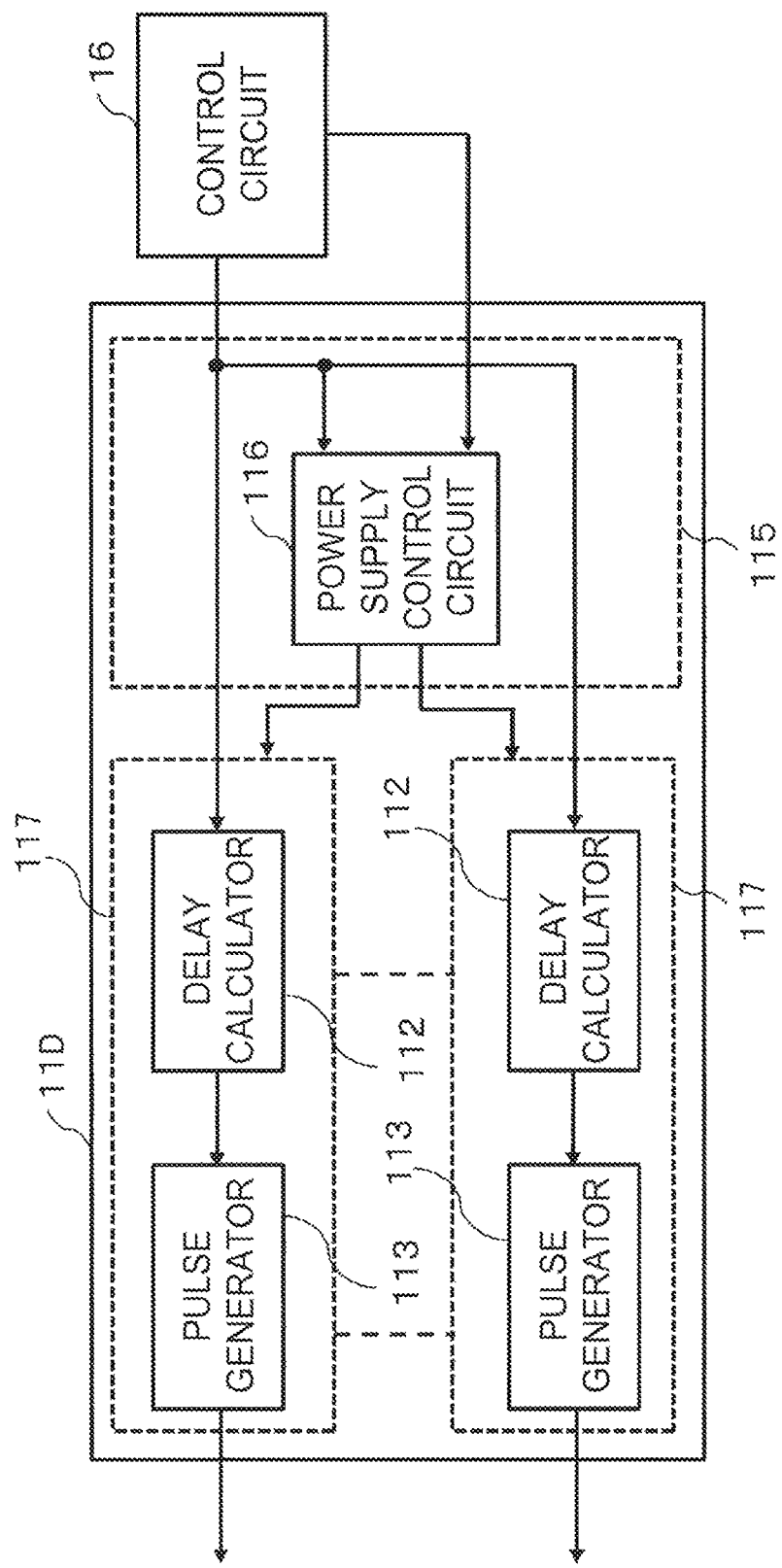

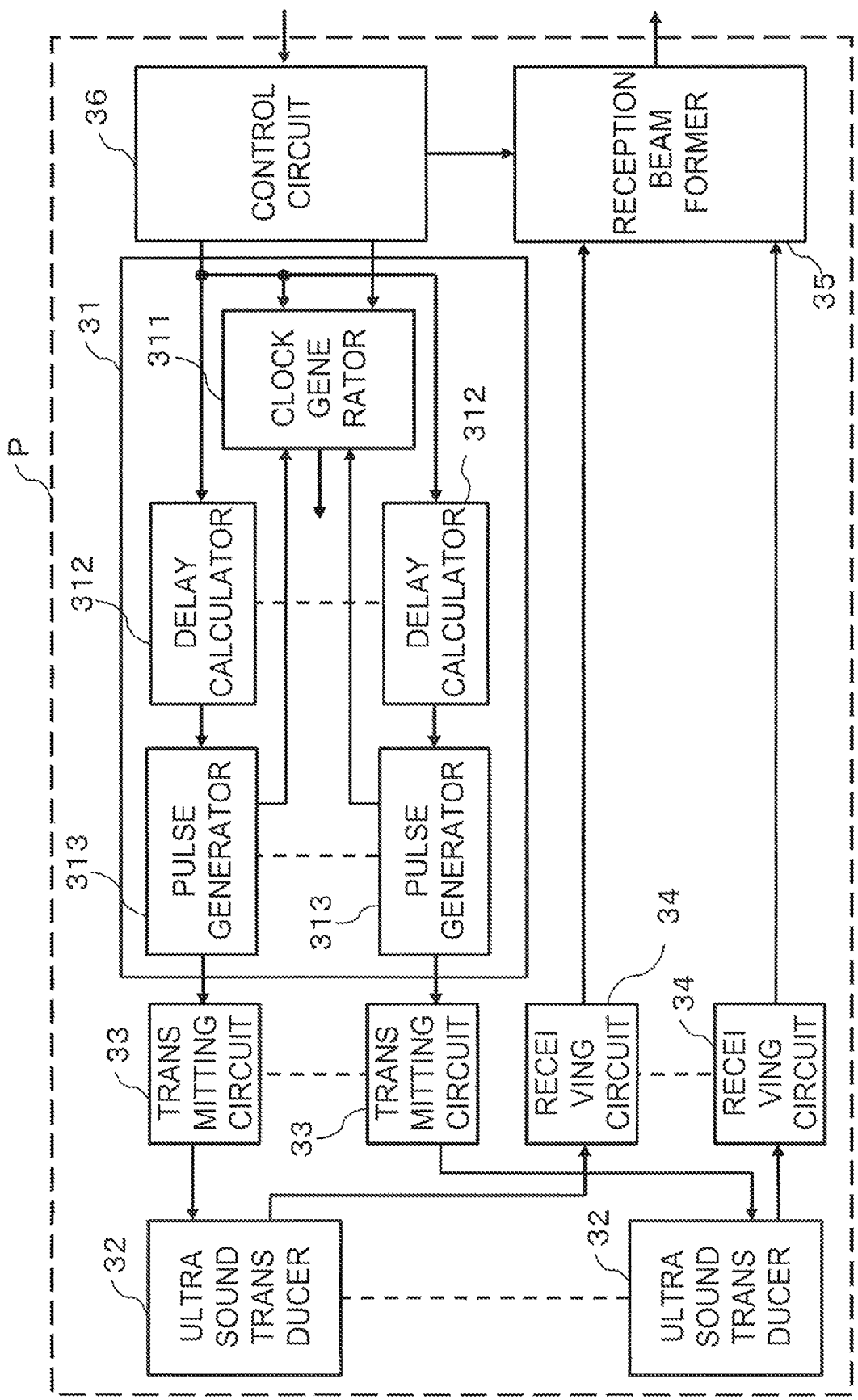

ULTRASOUND DIAGNOSIS APPARATUS AND ULTRASOUND PROBE

CROSS-REFERENCE TO RELATED APPLICATION

This application is based upon and claims the benefit of priority from Japanese Patent Applications No. 2016-244060, filed on Dec. 16, 2016 and No. 2017-221480, filed on Nov. 17, 2017; the entire contents of which are incorporated herein by reference.

FIELD

Embodiments described herein relate generally to an ultrasound diagnosis apparatus and an ultrasound probe.

BACKGROUND

In the medical field, the ultrasound diagnosis apparatus is used for various diagnoses and treatments because it can examine the internal structure, blood flow state, and the like of the subject non-invasively. The ultrasound diagnosis apparatus transmits ultrasound waves into the subject's body from an ultrasound probe having a ultrasound transducer (piezoelectric transducer) at its tip and brought into contact with the body surface of the subject. Then, the transducer of the ultrasound probe receives reflected waves caused by the acoustic impedance mismatch inside the subject. The ultrasound diagnosis apparatus generates an ultrasound image based on the received signal obtained in this manner.

A signal applied to the ultrasound transducer to drive it is generated by a transmission beam former. The transmission beam former is a circuit that calculates a delay corresponding to the distance between each of ultrasound transducers and a focal point such that the phases of ultrasound waves transmitted from the ultrasound transducers to the subject are aligned at a predetermined focal point in the subject and generates a transmission pulse to which the delay is added. Therefore, the transmission beam former is provided with a delay calculator and a pulse generator therein. After the delay is added by the delay calculator or the pulse generator, the transmission pulse is generated.

When transmitting ultrasound waves and receiving reflected waves, the ultrasound probe performs time division to alternately transmits the ultrasound signals and receives the reflected waves. Therefore, while receiving the reflected waves, the transmission beam former does not generate the transmission pulse and stops its operation.

Even when receiving the reflected waves, the transmission beam former is supplied with a clock. That is, the transmission beam former is always supplied with the clock regardless of whether it is transmitting ultrasound signals or receiving reflected waves. In this manner, when the clock is always supplied to the transmission beam former, the power consumption of, for example, the ultrasound diagnosis apparatus or the ultrasound probe provided with the transmission beam former becomes large.

For this reason, there have been proposed various methods regarding the reduction of power consumption in the ultrasound diagnosis apparatus or the ultrasound probe.

BRIEF DESCRIPTION OF THE DRAWINGS

FIG. 12 is a block diagram illustrating another configuration of the transmission beam former of the fourth embodiment.

FIG. 13 is a block diagram illustrating a configuration of an ultrasound probe according to a fifth embodiment.

DETAILED DESCRIPTION

In general, according to one embodiment, an ultrasound diagnosis apparatus includes a transmission beam former and a transmitting circuit. The transmission beam former generates a transmission pulse. The transmitting circuit supplies an ultrasound transducer with the transmission pulse received from the transmission beam former as a drive signal. The supply of a clock necessary for the generation of the transmission pulse is stopped during a substantial reception period of echo signals from the ultrasound transducer.

First Embodiment

A first embodiment will be described below with reference to the drawings.

[Configuration of Ultrasound Diagnosis Apparatus and Ultrasound Probe]

Figure 1:
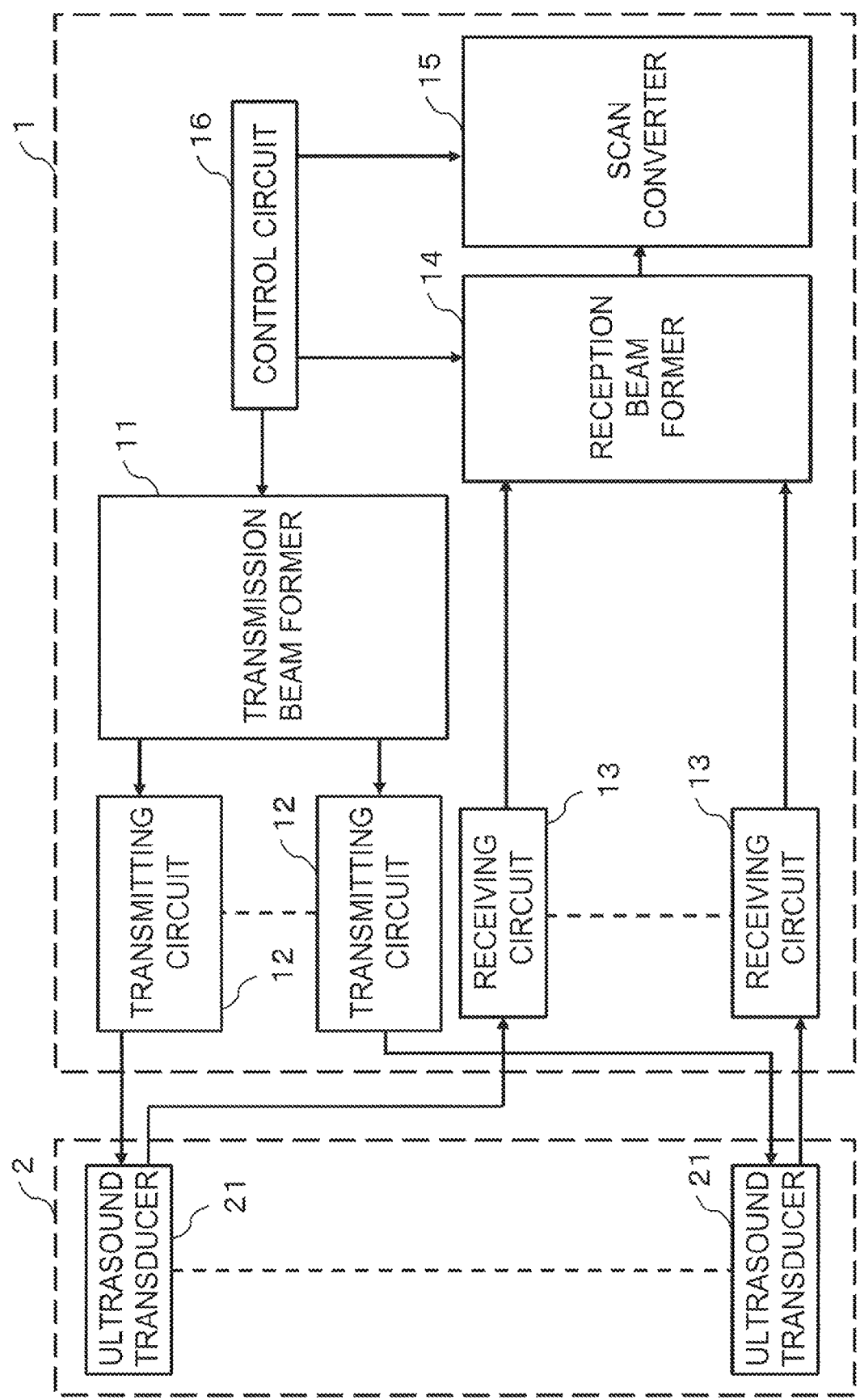
FIG. 1 is a block diagram illustrating a configuration of an ultrasound diagnosis apparatus and an ultrasound probe according to a first embodiment.

FIG. 1 is a block diagram illustrating the internal configuration of an ultrasound diagnosis apparatus 1 and an ultrasound probe 2 according to a first embodiment. In the first to fourth embodiments (the second to fourth embodiments will be described later), the ultrasound probe 2 is detachably connected to the ultrasound diagnosis apparatus 1.

The ultrasound diagnosis apparatus 1 includes a transmission beam former 11 configured to generate a transmission pulse, a transmitting circuit 12 configured to supply a drive signal to ultrasound transducers 21 in the ultrasound probe 2, a receiving circuit 13 configured to receive a reflection signal from the ultrasound probe 2, a reception beam former 14 configured to process the reflection signal, a scan converter 15 configured to generate an ultrasound image, and a control circuit 16 configured to control each unit.

Note that, while the configuration of the ultrasound diagnosis apparatus 1 of the first embodiment has been described above, it is only the configuration supposed to be necessary for explaining the first embodiment. Accordingly, although not illustrated in FIG. 1, the ultrasound diagnosis apparatus 1 may further include such a configuration as an input circuit which is operated by an operator such as an examiner and a display controller for displaying ultrasound images generated.

The transmission beam former 11 generates a transmission pulse under the control of the control circuit 16, and outputs it to the transmitting circuit 12. As will be described later, the transmission pulse is a drive signal applied from the transmitting circuit 12 to the ultrasound transducers 21. The transmission beam former 11 calculates a delay corresponding to the distance between each of the ultrasound transducers 21 and a focal point such that the phases of ultrasound waves transmitted from the ultrasound transducers 21 to the subject are aligned at a predetermined focal point in the subject and generates a transmission pulse (drive signal) to which the delay is added.

Figure 2:
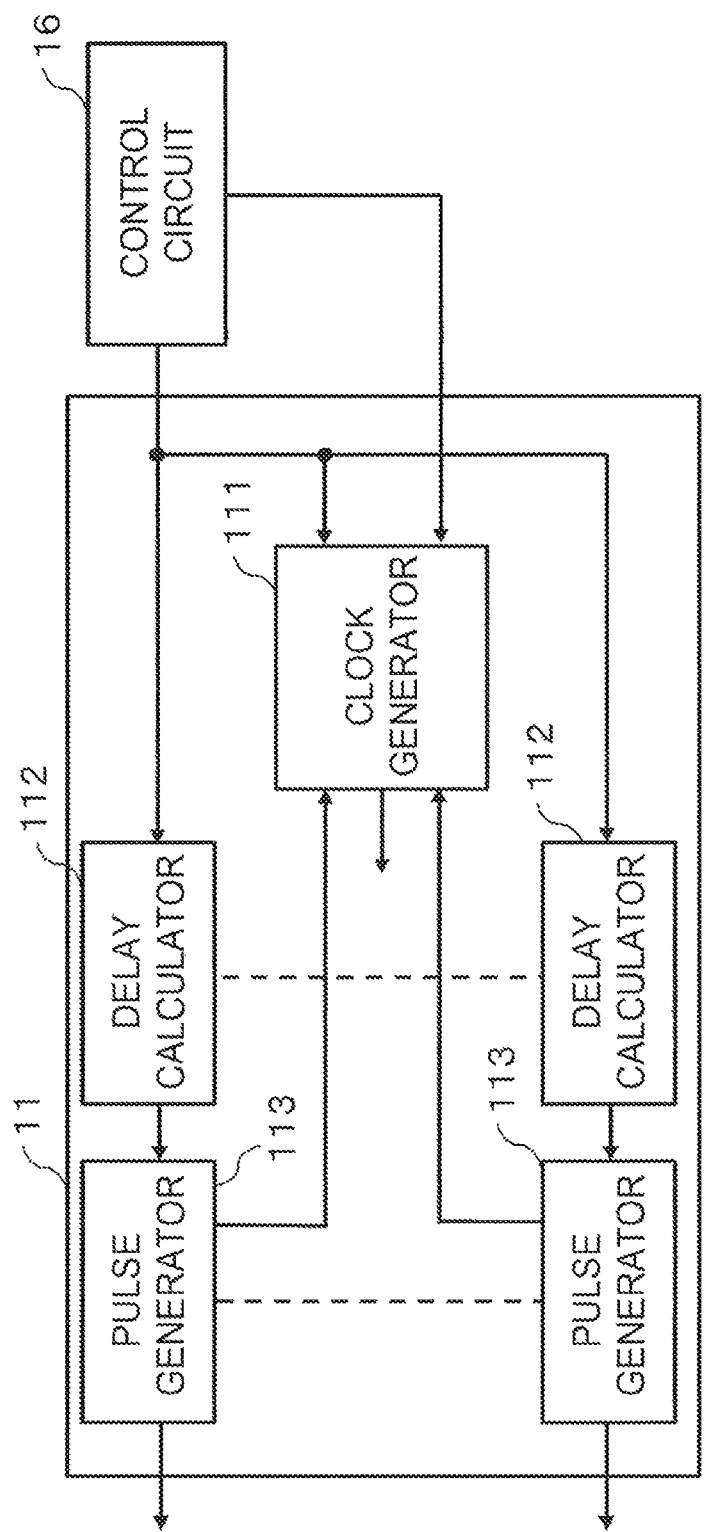
FIG. 2 is a block diagram illustrating a configuration of a transmission beam former of the first embodiment.

FIG. 2 is a block diagram illustrating a configuration of the transmission beam former 11 of the first embodiment. The transmission beam former 11 includes a clock generator 111, a delay calculator 112, and a pulse generator 113. The clock generator 111 receives a transmission synchronization signal and a transmission clock from the control circuit 16, and generates a clock to be supplied to the delay calculator 112. The delay calculator 112 calculates a delay to be added to each transmission pulse. The pulse generator 113 generates a transmission pulse to be supplied to the transmitting circuit 12. The transmission pulse supplied from the pulse generator 113 to the transmitting circuit 12 is applied to the ultrasound transducers 21 of the ultrasound probe 2 as a drive signal.

FIG. 2 illustrates one clock generator (111) in the transmission beam former 11. A combination of the delay calculator 112 and the pulse generator 113 is provided with respect to each channel of the ultrasound transducers 21. There are a plurality of channels, and a plurality of the delay calculators 112 and the pulse generators 113 are provided in the transmission beam former 11. However, in FIG. 2, only two pairs of the delay calculator 112 and the pulse generator 113 are illustrated, and others are not illustrated.

Referring back to FIG. 1, the transmitting circuit 12 receives the transmission pulse generated by the transmission beam former 11, and transmits it to the ultrasound transducers 21 as a drive signal for generating ultrasound waves in the ultrasound probe 2. As a configuration of the transmitting circuit 12, for example, the configuration of a switch pulser or a linear driver can be employed.

The receiving circuit 13 receives a reflection signal (echo signal) from the ultrasound probe 2. The echo signal received by the receiving circuit 13 is fed to the reception beam former 14. The reception beam former 14 adds a delay to the echo signal, and outputs the signal acquired by the delay addition to the scan converter 15.

The scan converter 15 generates various data by using the signal supplied from the reception beam former 14. The scan converter 15 includes, for example, a B mode processing circuit, a Doppler mode processing circuit, a color Doppler mode processing circuit, and the like (not illustrated). The B mode processing circuit visualizes the amplitude information of the received signal and generates B mode signal data. The Doppler mode processing circuit extracts a Doppler shift frequency component from the received signal, and applies the fast Fourier transform (FFT) and the like to generate Doppler signal data of blood flow information. The color Doppler mode processing circuit visualizes the blood flow information based on the received signal and generates color Doppler mode signal data.

Further, the scan converter 15 generates Doppler images and ultrasound images such as a two-dimensional cross section and a rendering image of the scan area based on the data generated. For example, the scan converter 15 generates volume data on the scan area from the data supplied. Then, the scan converter 15 generates two-dimensional ultrasound image data and volume rendering image data by multi-sectional reconstruction or multi-planar reconstruction (MPR) based on the volume data generated. The scan converter 15 outputs one or more of the above ultrasound images to a display circuit (not illustrated).

The ultrasound probe 2 transmits and receives ultrasound waves in a state where its distal end surface is in contact with the surface of the subject. The ultrasound probe 2 incorporates a plurality of the ultrasound transducers 21, which are one-dimensionally arranged on the distal end surface. The ultrasound probe 2 transmits ultrasound waves to the inside of the subject by each of the ultrasound transducers 21 to scan the scan area, and receives reflected waves from the subject as echo signals. Examples of the scan include various scans such as B mode scan and Doppler mode scan.

In addition, examples of the ultrasound probe 2 include a sector scan probe, a linear scan probe, a convex scan probe, and the like. Any of these probes is arbitrarily selected according to an area to be diagnosed. The ultrasound transducers 21 need not necessarily be arranged one-dimensionally. If the ultrasound transducers 21 are arranged two-dimensionally, volume data can be acquired in real time. In the case of obtaining a three-dimensional stereoscopic image, a three-dimensional scanning probe is used as the ultrasound probe 2. A two-dimensional array probe or a mechanical four-dimensional probe can be cited as an example of the three-dimensional scanning probe.

FIG. 1 does not illustrate all of the ultrasound transducers 21 built in the ultrasound probe 2. FIG. 1 illustrate only two ultrasound transducers (21), and the illustration of others is omitted by a broken line provided between the two ultrasound transducers 21.

[Operation of Transmission Beam Former and Signal Flow]

Figure 3:
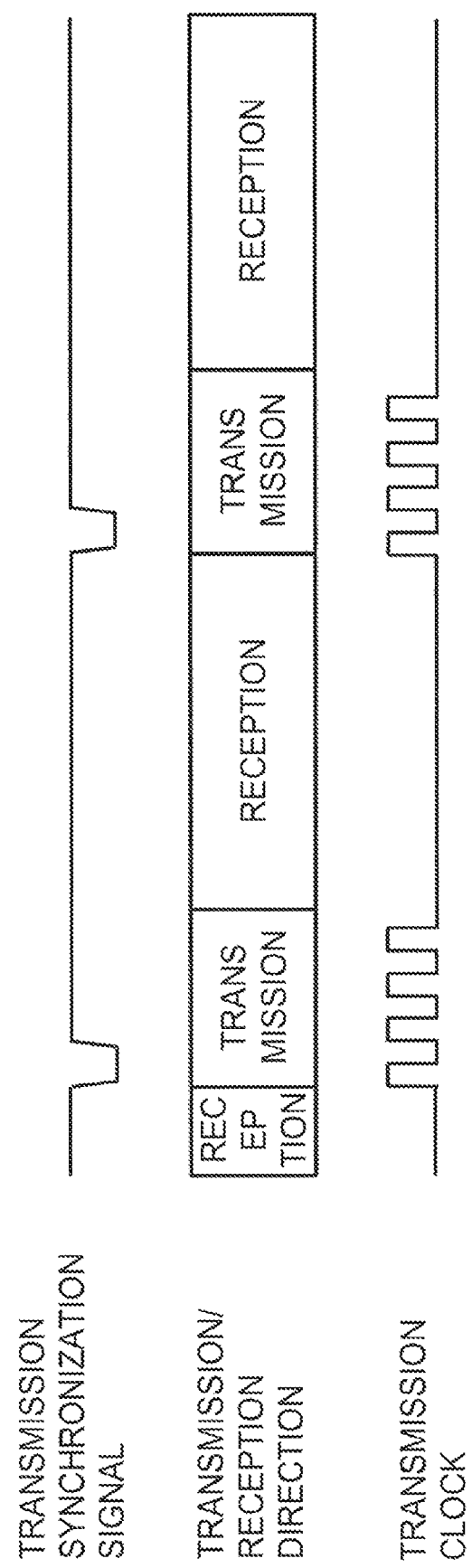
FIG. 3 is a waveform diagram illustrating the state of the supply of a transmission clock to the transmission beam former in the first embodiment.

Next, with reference to FIGS. 2 and 3, a description will be given of the operation of the transmission beam former and a signal flow. FIG. 3 is a waveform diagram illustrating the state of the supply of a transmission clock to the transmission beam former 11 in the first embodiment.

As described above, the transmission beam former 11 generates a transmission pulse (drive signal) to be applied to the ultrasound transducers 21. First, the clock generator 111 is fed with a transmission synchronization signal and a transmission clock from the control circuit 16. Not only the clock generator 111 but also the delay calculator 112 of each channel is fed with the transmission synchronization signal from the control circuit 16.

The clock generator 111 supplies the transmission clock to each of the delay calculators 112 and the pulse generators 113 when the ultrasound probe 2 enters a period for transmitting ultrasound waves (transmission waves) to the subject therefrom. The clock generator 111 supplies the transmission clock concurrently to all the delay calculators 112 in the transmission beam former 11.

Upon receipt of the transmission clock from the clock generator 111, each of the delay calculators 112 calculates a delay to be added to a transmission pulse. The delay calculator 112 supplies a pulse generation trigger including the delay to the pulse generator 113 connected thereto.

The pulse generator 113 generates a transmission pulse to be supplied to the transmitting circuit 12 by adding thereto the delay received from the delay calculator 112. As described above, the transmission pulse generated is applied to the ultrasound transducers 21 through the transmitting circuit 12.

An example is given above in which the pulse generator 113 generates the transmission pulse by adding thereto the delay calculated by the delay calculator 112; however, it is not so limited. For example, the pulse generation trigger supplied to the pulse generator 113 may be delayed.

The ultrasound probe 2 alternately performs the transmission of ultrasound waves to the subject and the receipt of reflected waves. Accordingly, a transmission period for transmitting ultrasound waves and a reception period for receiving reflected waves are alternately provided. The transmission pulse generated by the transmission beam former 11 is applied to the ultrasound transducers 21 during the transmission period. When the control circuit 16 switches the transmission period to the reception period, the application of the transmission pulse to the ultrasound transducers 21 is terminated.

Having transmitted the transmission pulse generated to the transmitting circuit 12, the pulse generator 113 transmits a transmission completion signal to the clock generator 111. In FIG. 2, an arrow extending from the pulse generator 113 to the clock generator 111 represents the transmission completion signal transmitted from the pulse generator 113 to the clock generator 111. Upon receipt of the transmission completion signal transmitted from all the pulse generators 113, the clock generator 111 stops the supply of the transmission clock to the delay calculators 112.

The waveform diagram of FIG. 3 illustrates "transmission/reception direction" indicating "transmission" and "reception". The "transmission/reception direction" indicates the transmission of ultrasound waves and the receipt of reflected waves in the ultrasound probe 2. The lengths of "transmission" and "reception" indicated by the "transmission/reception direction" correspond to the lengths of the "transmission period" and the "reception period". Two waveform diagrams are illustrated above and below the "transmission/reception direction" in the center. A waveform diagram of the "transmission synchronization signal" is illustrated above the "transmission/reception direction". Meanwhile, a waveform diagram of the transmission clock supplied from the clock generator 111 to the delay calculator 112 is illustrated below the "transmission/reception direction".

As described above, the control circuit 16 feeds a transmission synchronization signal to the clock generator 111 and each of the delay calculators 112. The control circuit 16 also feeds a transmission clock to the clock generator 111, and the transmission clock is supplied to the delay calculator 112. Referring to the waveform diagram of the transmission clock, the transmission clock is supplied from the clock generator 111 to each of the delay calculators 112. From here the transmission period begins.

Then, the transmission/reception direction of ultrasound waves changes. The clock generator 111 stops the supply of the transmission clock to each of the delay calculators 112 immediately before the transmission period is switched to the reception period. Thereafter, the transmission clock is not supplied to each of the delay calculators 112 during the reception period until the transmission period starts again.

That is, as indicated by the waveform of the transmission clock in FIG. 3, when the reception period is switched to the transmission period, the transmission clock is supplied from the clock generator 111 to each of the delay calculators 112. The clock generator 111 stops the supply of the transmission clock to each of the delay calculators 112 immediately before the transmission period is switched to the reception period.

Although it is rare, the transmission clock may be supplied to the delay calculators 112 once twice after the transmission period is switched to the reception period. However, even if this happens, it is insignificant with respect to the length of the reception period, and does not impair the operation of the ultrasound diagnosis apparatus or the purpose of this embodiment such as reduction in the power consumption of the ultrasound diagnosis apparatus. Even if the supply of the transmission clock is continued only for a predetermined period for some reason after the transmission period is switched to the reception period, this does not hinder the effect of suppressing the power consumption. The same applies to the embodiments described later.

In FIG. 2, one arrow is illustrated from the clock generator 111 toward the left side. This arrow indicates that all the delay calculators are simultaneously supplied with a transmission clock, and the supply of the transmission clock is stopped at the same time for all the delay calculators.

Figure 4:
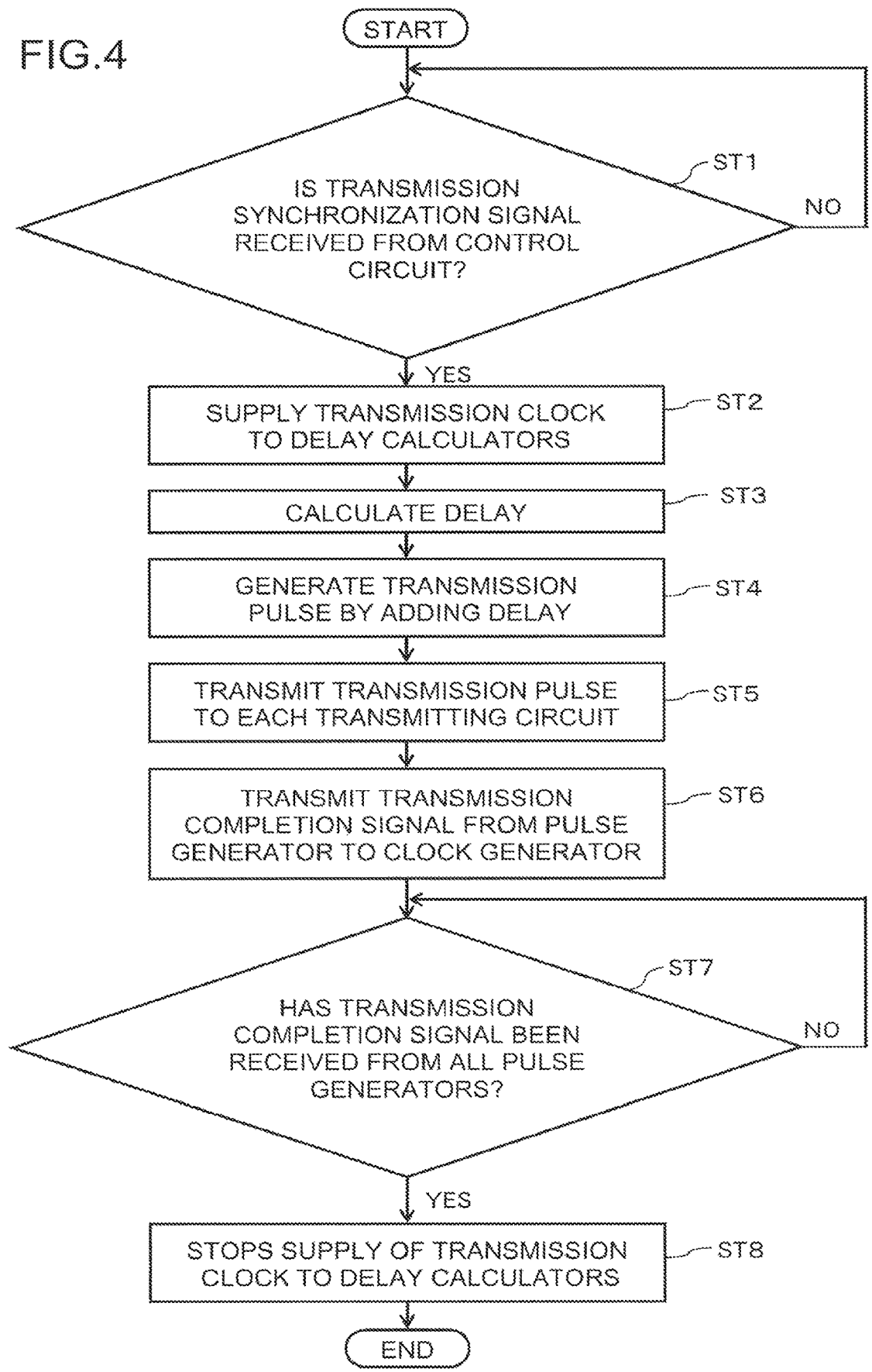
FIG. 4 is a flowchart illustrating the operation of supplying a transmission clock to the transmission beam former in the first embodiment.

FIG. 4 is a flowchart illustrating the operation of supplying a transmission clock to the transmission beam former 11 in the first embodiment. First, the transmission beam former 11 determines whether a transmission synchronization signal is received from the control circuit 16 (ST1). The transmission beam former 11 stands by until it receives a transmission synchronization signal from the control circuit 16 (NO in ST1).

Having received a transmission synchronization signal from the control circuit 16 (YES in ST1), the clock generator 111 supplies a transmission clock to the delay calculators 112 of all the channels (ST2). When supplied with the transmission clock, each of the delay calculators 112 calculates a delay to be added to a transmission pulse (ST3).

The delay calculated is supplied to each of the pulse generators 113. The pulse generator 113 generates a transmission pulse by adding the delay thereto (ST4). Then, the pulse generator 113 transmits the transmission pulse to the transmitting circuit 12 (ST5).

The pulse generator 113 transmits, to the clock generator 111, a signal for completion of the transmission of the transmission pulse (transmission completion signal) to the transmitting circuit 12 (ST6). The clock generator 111 determines whether the transmission completion signal has been received from all the pulse generators 113 (ST7).

When the transmission completion signal has not been received from all the pulse generators 113 (NO in ST7), the clock generator 111 waits until it receives the transmission completion signal from all the pulse generators 113. On the other hand, when the clock generator 111 determines that the transmission completion signal has been received from all the pulse generators 113 (YES in ST7), the clock generator 111 stops the supply of the transmission clock to all the delay calculators 112 (ST8).

As described above, when the transmission completion signal is transmitted from all the pulse generators 113, the transmission/reception direction is changed in the ultrasound probe 2. At this time, the transmission period is switched to the reception period. The transmission clock is not supplied to the delay calculators 112 until a transmission synchronization signal is fed again to the clock generator 111 (the transmission beam former 11).

As described above, according to this embodiment, the clock generator supplies a transmission clock to the delay calculator only in the transmission period, and stops the supply of the clock during the substantial reception period of echo signals, differently from conventional technologies in which the clock generator supplies a transmission clock to the delay calculator regardless of the transmission period and the reception period. With this, the power consumption in the ultrasound diagnosis apparatus can be reduced. Thus, it is possible to achieve various effects such as the miniaturization of constituent equipment, the integration of channels, and the reduction of noise due to the fluctuation of the power supply voltage. As a result, the ultrasound diagnosis apparatus can be downsized.

Second Embodiment

Next, a second embodiment will be described. In the second embodiment, like reference numerals designate the same constituent elements as those described in the first embodiment, and the same description will not be repeated.

In the first embodiment, the clock generator 111 simultaneously supplies a transmission clock to all of the delay calculators 112. For this reason, the transmission beam former 11 as a whole supplies the transmission clock during the transmission period. Meanwhile, the supply of the transmission clock is stopped during the substantial reception period of echo signals.

In the second embodiment, the transmission beam former 11 performs control such that the transmission clock is supplied or the supply of the transmission clock is stopped for each channel. The clock generator 111 sequentially stops the supply of the transmission clock from the channel where the transmission pulse has been supplied to the transmitting circuit 12.

[Configuration of Transmission Beam Former]

Figure 5:
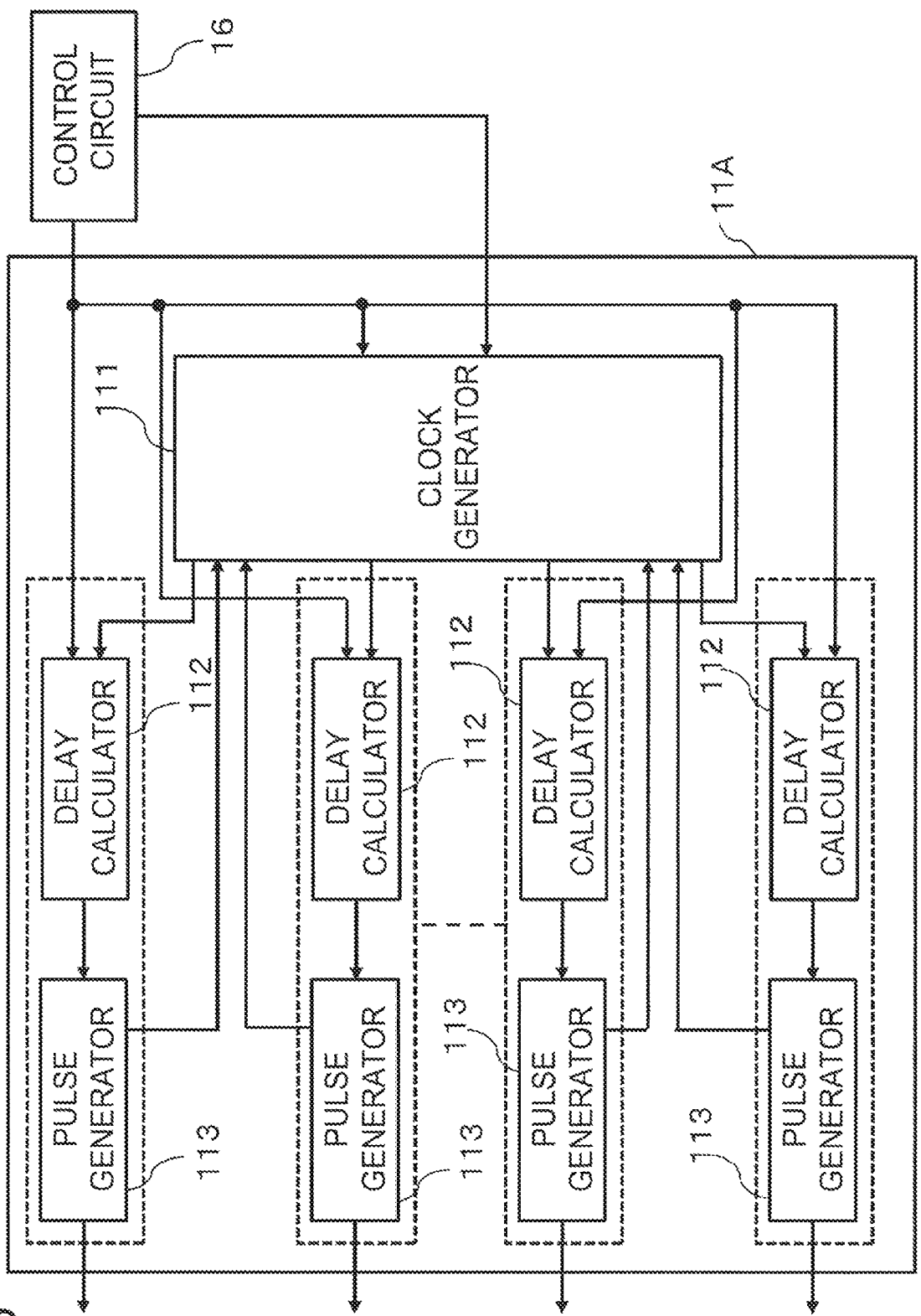
FIG. 5 is a block diagram illustrating a configuration of a transmission beam former according to a second embodiment.
Figure 6:
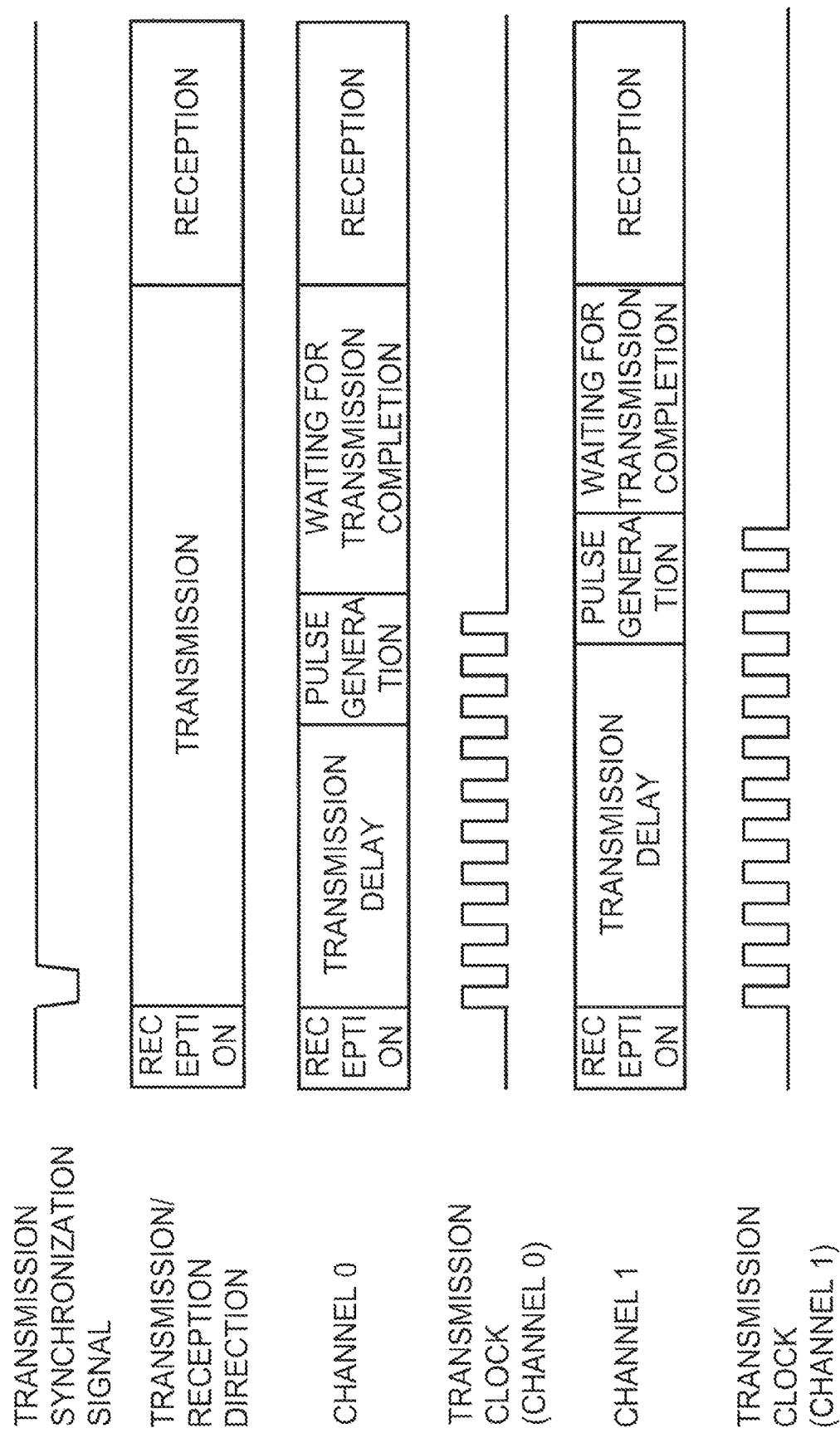
FIG. 6 is a waveform diagram illustrating the state of the supply of a transmission clock to the transmission beam former in the second embodiment.

FIG. 5 is a block diagram illustrating a configuration of a transmission beam former 11A according to the second embodiment. FIG. 6 is a waveform diagram illustrating the state of the supply of a transmission clock to the transmission beam former 11A in the second embodiment.

The transmission beam former 11A of the second embodiment has the same configuration as that of the first embodiment. However, the supply of the transmission clock from the clock generator 111 to the delay calculator 112 is stopped with respect to each channel. In FIG. 5, an arrow that indicates the supply of a transmission clock is illustrated for each of the delay calculators 112 of each channel and extends from the clock generator 111 to one of the delay calculators 112. Besides, in FIG. 5, in order to indicate that the delay calculator 112 and the pulse generator 113 are provided for each channel, these are surrounded by a broken line with respect to each channel. Incidentally, FIG. 5 does not illustrate an arrow indicating a clock supplied from the clock generator 111 to the pulse generator 113.

[Operation of Transmission Beam Former and Signal Flow]

In the second embodiment, the control circuit 16 feeds a transmission synchronization signal to the clock generator 111 and the delay calculators 112, and the transmission clock sent from the control circuit 16 to the clock generator 111 is supplied to the delay calculators 112 in the same manner as described in the first embodiment. Further, the clock generator 111 stops the supply of the transmission clock to each of the delay calculators 112 during the reception period in the same manner as the first embodiment.

However, the second embodiment differs from the first embodiment in that, when the transmission period is switched to the reception period, the supply of the transmission clock from the clock generator 111 to each of the delay calculators 112 is not stopped all at once and it is determined whether to stop the supply of the transmission clock is stopped for with respect to each channel before the transmission period is switched to the reception period.

FIG. 6 illustrates the waveform of the "transmission synchronization signal" and the "transmission/reception direction" of ultrasound waves from above. FIG. 6 also illustrates the operation of the transmission beam former 11A in the two channels of "Channel 0" and "Channel 1", and waveforms indicating a transmission clock which is supplied to the process below the "transmission/reception direction".

As illustrated in FIG. 5, the delay calculator and the pulse generator are provided for each of a plurality of channels in the transmission beam former 11A. FIG. 6 illustrates only two channels and the process performed in the channels.

In FIG. 6, "reception", "transmission delay", "pulse generation", "waiting for transmission completion", and "reception" are illustrated in this order from the left on the side of the "channel 0". The term "reception" refers to the reception period in the "transmission/reception direction". Others, i.e., "transmission delay", "pulse generation", and "waiting for transmission completion" indicate processes performed in the transmission beam former 11A during the transmission period. Below these is the waveform of the transmission clock.

The "transmission delay" is a process performed in the delay calculator 112, and the "pulse generation" is a process performed in the pulse generator 113. Having transmitted a transmission pulse to the transmitting circuit 12, the pulse generator 113 sends a transmission completion signal to the clock generator 111. Therefore, the clock generator 111 is "waiting for transmission completion" until the pulse generation is completed and the transmission period is switched to the reception period.

The "Channel 1" is illustrated in the same manner as the "channel 0"; however, the time taken for each process performed during the transmission period is different. The "transmission delay" process in the channel 1 takes longer than the "transmission delay" process in the channel 0. As a result, the time of "waiting for transmission completion" in the channel 1 is shorter than that in the channel 0.

The clock generator 111 supplies a transmission clock to the delay calculator 112 until the signal of transmission completion is received from the pulse generator 113. As indicated by the waveform of the transmission clock in FIG. 6, with respect to both the channel 0 and the channel 1, the clock generator 111 supplies a transmission clock to the delay calculators 112 and the pulse generators 113 until the delay calculators 112 complete the process, the pulse generators 113 generate a pulse, and the transmission pulse is sent to the transmitting circuit 12.

However, a delay added to the transmission pulse generated by the pulse generator 113 varies depending on each channel. This can be seen in the difference in the length of "transmission delay" between the channel 0 and the channel 1 in FIG. 6 as described above. That is, the time during which the clock generator 111 supplies a transmission clock to each of the delay calculators 112 varies.

As described above, the time for which the transmission clock is supplied varies depending on each channel. Accordingly, the transmission time for transmitting a signal, which indicates that the pulse generator 113 has transmitted a transmission pulse to the clock generator 111, to the transmitting circuit 12 also varies depending on each channel. Thus, the clock generator 111 stops the supply of the transmission clock to the delay calculators 112 differently for each channel.

Figure 7:
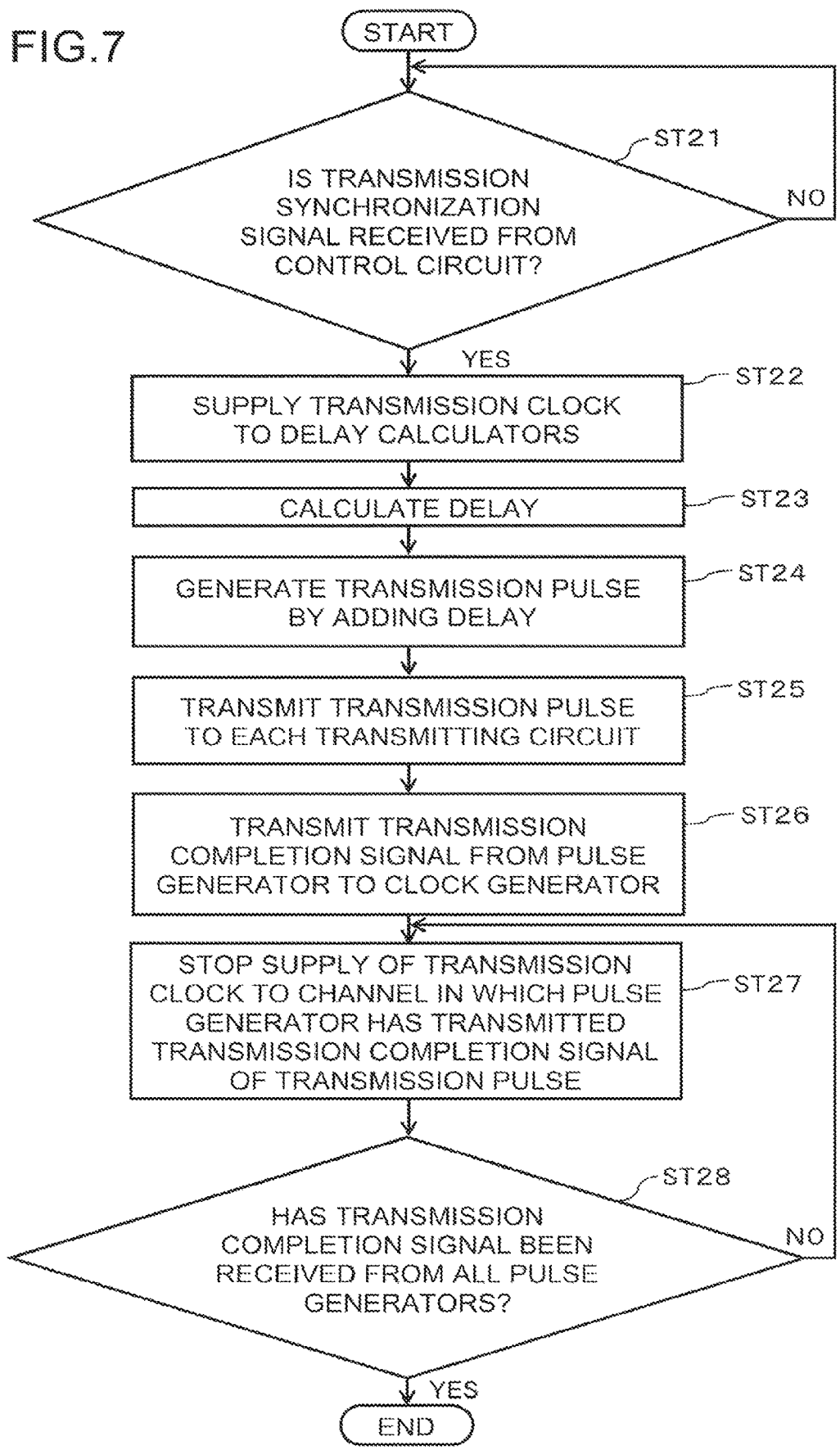
FIG. 7 is a flowchart illustrating the operation of supplying a transmission clock to the transmission beam former in the second embodiment.

FIG. 7 is a flowchart illustrating the operation of supplying a transmission clock to the transmission beam former 11A in the second embodiment. In FIG. 7, steps ST21 to ST26 are the same as steps ST1 to ST6 described in the first embodiment.

That is, the transmission beam former 11A determines whether a transmission synchronization signal is received from the control circuit 16 (ST21). The transmission beam former 11A stands by until it receives a transmission synchronization signal from the control circuit 16 (NO in ST21).

Having received a transmission synchronization signal from the control circuit 16 (YES in ST21), the clock generator 111 supplies a transmission clock to the delay calculators 112 of all the channels (ST22). When supplied with the transmission clock, each of the delay calculators 112 calculates a delay to be added to a transmission pulse (ST23).

The delay calculated is supplied to each of the pulse generators 113. The pulse generator 113 generates a transmission pulse by adding the delay thereto (ST24). Then, the pulse generator 113 transmits the transmission pulse to the transmitting circuit 12 (ST25). The pulse generator 113 transmits, to the clock generator 111, a transmission completion signal of the transmission pulse to the transmitting circuit 12 (ST26).

The clock generator 111 stops the supply of the transmission clock to the channel in which the pulse generator 113 has transmitted a transmission completion signal of the transmission pulse (ST27). As described above, the transmission completion signal is sent to the clock generator 111 at different times depending on the channels. Thus, the clock generator 111 stops the supply of the transmission clock sequentially from the channel from which the transmission completion signal has been received.

Then, the clock generator 111 determines whether the transmission completion signal has been received from all the pulse generators 113 (ST28).

When the transmission completion signal has been received from all the pulse generators 113 (YES in ST28), the clock generator 111 stops the supply of the transmission clock to all the delay calculators 112. The transmission clock is not supplied to the delay calculators 112 until a transmission synchronization signal is fed again to the clock generator 111 (the transmission beam former 11A) On the other hand, having determined that the transmission completion signal has not been received from all the pulse generators 113 (NO in ST28), the clock generator 111 stands by until it receives the transmission completion signal from the pulse generator 113 of each channel.

As described above, according to this embodiment, the clock generator supplies a transmission clock to the delay calculator only in the transmission period, and stops the supply of the clock during the substantial reception period of echo signals, differently from conventional technologies in which the transmission clock is supplied regardless of the transmission period and the reception period. With this, the power consumption in the ultrasound diagnosis apparatus can be reduced. Thus, it is possible to achieve various effects such as the miniaturization of constituent equipment, the integration of channels, and the reduction of noise due to the fluctuation of the power supply voltage. As a result, the ultrasound diagnosis apparatus can be downsized.

Further, the supply of the transmission clock from the clock generator 111 to the delay calculator 112 is controlled with respect to each channel. With this process, the supply of the transmission clock can be stopped even if there is a channel in the transmission period. Thus, the power consumption can be further reduced.

Note that, depending on the examination mode such as, for example, CW mode, there may be a channel not used in the ultrasound probe. In this case, the transmission clock is not supplied to the channel, and the supply of the transmission clock can be stopped even in the transmission period while the examination mode is selected.

There may be a channel that does not perform transmission depending on the ultrasound probe when the number of ultrasound transducers is small. When there is such an unused channel, the transmission clock is not supplied to the channel, and the supply of the transmission clock can be stopped even during the transmission period.

Third Embodiment

Next, a third embodiment will be described. In the third embodiment, like reference numerals designate the same constituent elements as those described in the first and second embodiments, and the same description will not be repeated.

In the second embodiment, the supply of the transmission clock from the clock generator 111 to the delay calculator 112 and the stop thereof are controlled with respect to each channel. On the other hand, in the third embodiment, the supply of the transmission clock from the clock generator 111 and the stop thereof are controlled with respect to each of the delay calculators 112 and each of the pulse generators 113.

[Configuration of Transmission Beam Former]

Figure 8:
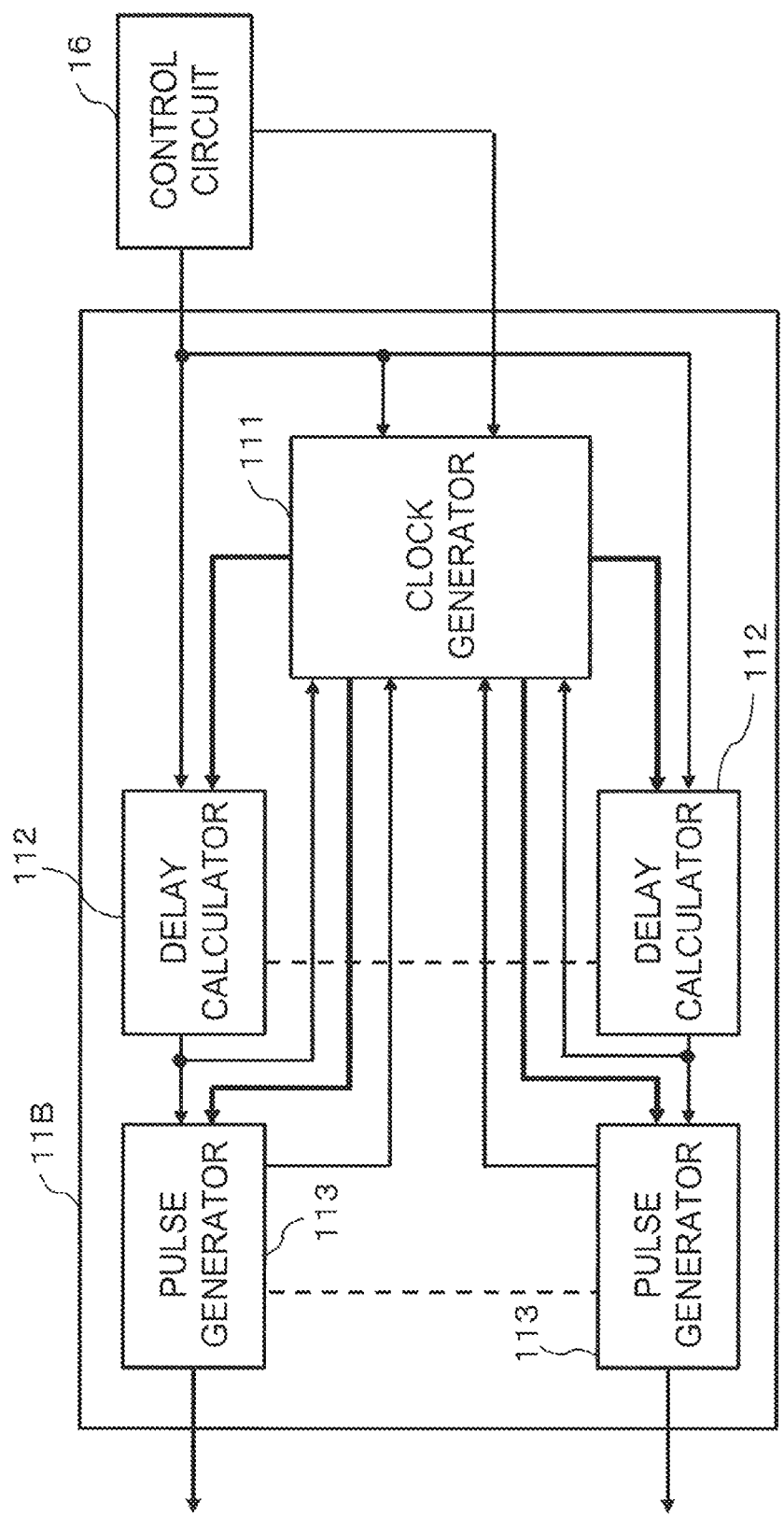
FIG. 8 is a block diagram illustrating a configuration of a transmission beam former according to a third embodiment.

FIG. 8 is a block diagram illustrating a configuration of a transmission beam former 11B according to the third embodiment. The transmission beam former 11B is provided with a signal line branched from a signal line, which connects the delay calculator 112 and the pulse generator 113, and connected to the clock generator 111, in addition to the internal configuration of the transmission beam former 11. In FIG. 8, an arrow indicates a signal sent from the delay calculator 112 to the clock generator 111 through the signal line.

Further, the pulse generator 113 is also connected to the clock generator 111 through a signal line. An arrow indicates a signal sent from the clock generator 111 to the pulse generator 113 through the signal line.

The delay calculator 112 sends the pulse generator 113 a pulse generation trigger including a delay to be added to a transmission pulse generated in the pulse generator 113. In the third embodiment, the clock generator 111 is also fed with the pulse generation trigger sent from the delay calculator 112. Besides, the clock generator 111 sends a pulse generation clock to the pulse generator 113.

[Operation of Transmission Beam Former and Signal Flow]

Figure 9:
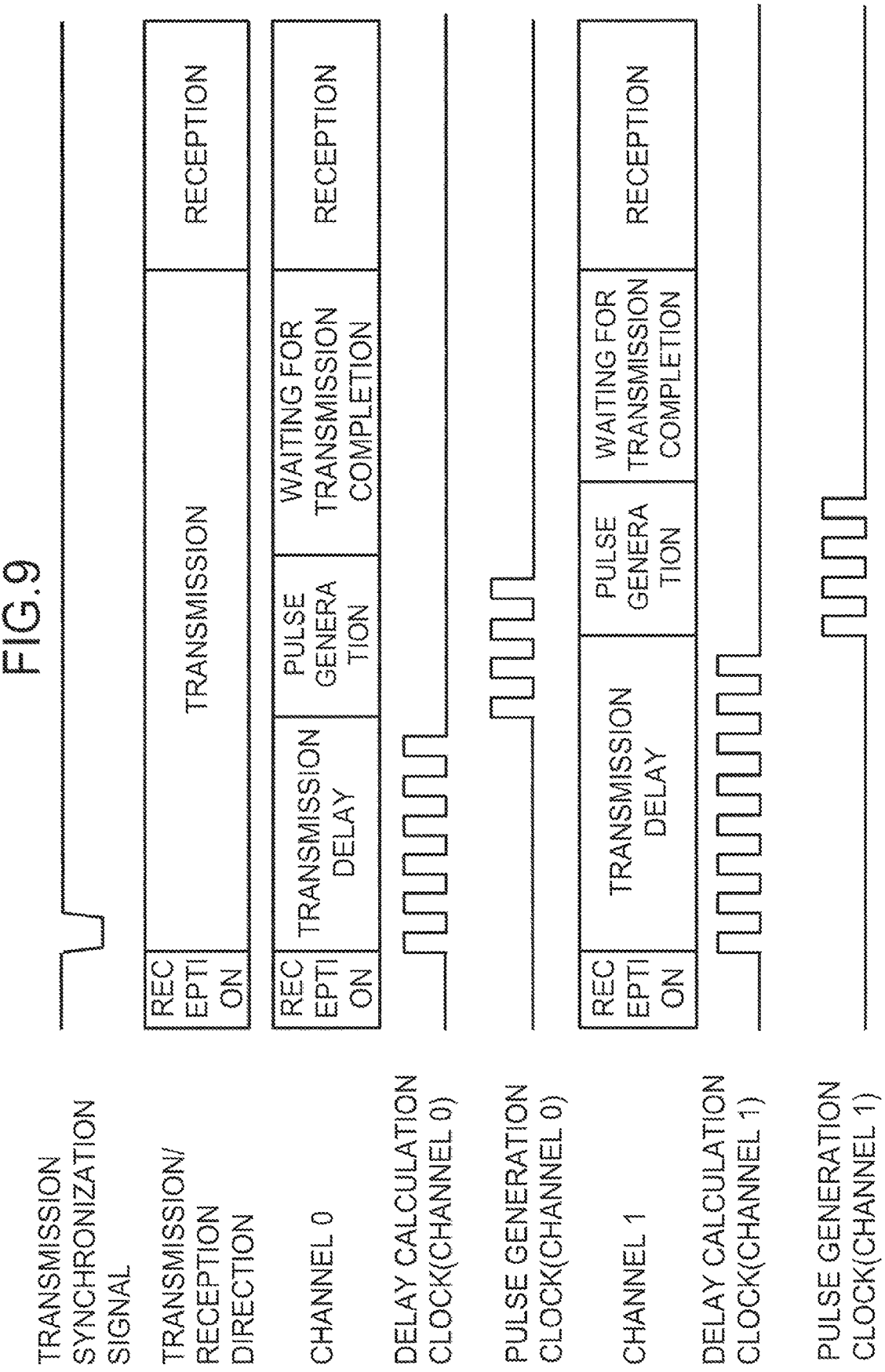
FIG. 9 is a waveform diagram illustrating the state of the supply of a transmission clock to the transmission beam former in the third embodiment.

Next, with reference to FIGS. 8 and 9, a description will be given of the operation of the transmission beam former 11B and a signal flow. FIG. 9 is a waveform diagram illustrating the state of the supply of a transmission clock to the transmission beam former 11B in the third embodiment.

FIG. 9 illustrates the waveform of the "transmission synchronization signal" and the "transmission/reception direction" of ultrasound waves from above as in the waveform diagrams (FIGS. 3 and 6) used in the description of the first and second embodiments. FIG. 9 also illustrates waveform diagrams of the "channel 0" and the "channel 1" below that.

Taking the waveform diagram of the "channel 0" as an example, "reception", "transmission delay", "pulse generation", "waiting for transmission completion", and "reception" are illustrated in this order from the left on the side of the "channel 0". The term "reception" refers to the reception period in the "transmission/reception direction". Others, i.e., "transmission delay", "pulse generation", and "waiting for transmission completion" indicate processes performed in the transmission beam former 11B during the transmission period.

In addition, below these is the waveform of the transmission clock supplied from the clock generator 111. Differently from the previous embodiments, "delay calculation clock" and "pulse generation clock" are illustrated separately. The "delay calculation clock" is a transmission clock supplied from the clock generator 111 to the delay calculator 112. The "pulse generation clock" is a transmission clock supplied from the clock generator 111 to the pulse generator 113.

In the transmission beam former 11B, the flow of each signal upon generation of a transmission pulse (drive signal) to be applied to the ultrasound transducers 21 is as follows. First, the clock generator 111 is fed with a transmission synchronization signal and a transmission clock from the control circuit 16. Not only the clock generator 111 but also the delay calculator 112 of each channel is fed with the transmission synchronization signal from the control circuit 16.

In the transmission period, the clock generator 111 supplies a delay calculation clock to each of the delay calculators 112. The clock generator 111 supplies the delay calculation clock to all the delay calculators 112 in the transmission beam former 11B all at once.

Upon receipt of the delay calculation clock from the clock generator 111, each of the delay calculators 112 calculates a delay to be added to each transmission pulse. The delay calculator 112 supplies a pulse generation trigger including the delay calculated to the pulse generator 113 connected thereto.

As described above, the pulse generation trigger sent from the delay calculator 112 to the pulse generator 113 is also sent to the clock generator 111. Upon receipt of the pulse generation trigger, the clock generator 111 first stops the supply of the delay calculation clock to the delay calculator 112.

The waveform diagram of FIG. 9 illustrates this flow. Taking the channel 0 as an example, when the reception period is switched to the transmission period, the clock generator 111 supplies a delay calculation clock to the delay calculator 112. While the delay calculator 112 is calculating a delay to be added to a transmission pulse (during the "transmission delay"), the clock generator 111 continuously supplies the delay calculation clock to the delay calculator 112. Then, the delay calculator 112 sends a pulse generation trigger to the pulse generator 113 and the clock generator 111.

Upon receipt of the pulse generation trigger from the delay calculator 112, the clock generator 111 stops supplying the delay calculation clock to the delay calculator 112. With reference to FIG. 9, the waveform of the "delay calculation clock" is illustrated only during the "transmission delay", and is not illustrated in the next "pulse generation" process of the pulse generator 113.

Having received the pulse generation trigger, the clock generator 111 supplies a pulse generation clock to the pulse generator 113. The pulse generator 113 generates a transmission pulse using the delayed pulse transmission trigger sent from the delay calculator 112 and the pulse generation clock supplied from the clock generator 111. FIG. 9 illustrates that the "pulse generation" process is started by the supply of the pulse generation clock from the clock generator 111 to the pulse generator 113.

As described above, the transmission pulse generated by the pulse generator 113 is applied to the ultrasound transducers 21 through the transmitting circuit 12.

Having transmitted the transmission pulse generated to the transmitting circuit 12, the pulse generator 113 sends a transmission completion signal to the clock generator 111. In FIG. 8, an arrow extending from the pulse generator 113 to the clock generator 111 represents the transmission completion signal sent from the pulse generator 113 to the clock generator 111. Upon receipt of the transmission completion signal from the pulse generator 113, the clock generator 111 stops supplying the pulse generation clock to the pulse generator 113 that has sent the transmission completion signal.

The waveform diagram of FIG. 9 illustrates this as follows. The waveform indicating the pulse generation clock is illustrated only during the "pulse generation" process. The waveform indicating the pulse generation clock is not illustrated when "waiting for transmission completion" is started after the pulse generation process is completed in the pulse generator 113 and a transmission completion signal is transmitted to the clock generator 111.

Figure 10:
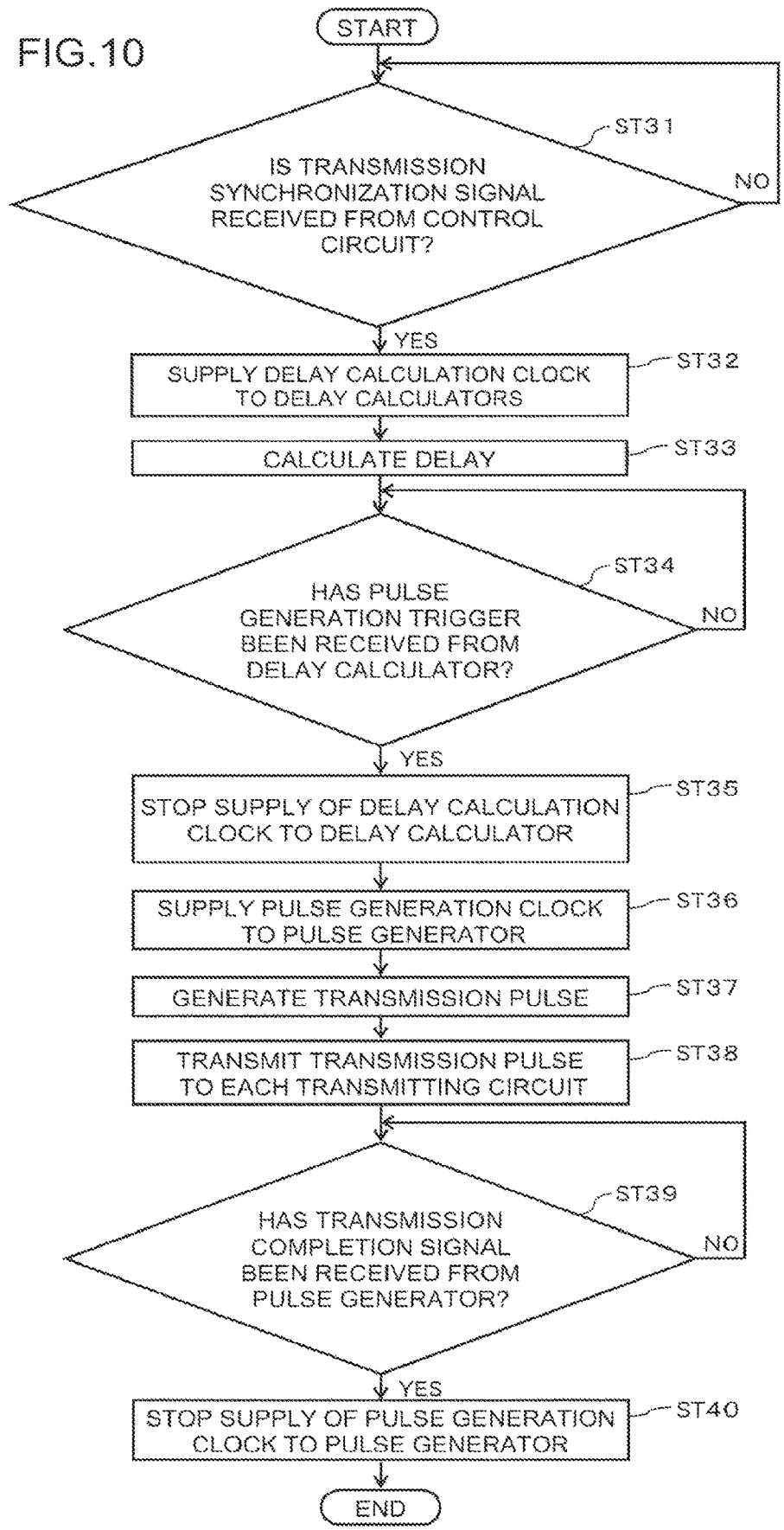
FIG. 10 is a flowchart illustrating the operation of supplying a transmission clock to the transmission beam former in the third embodiment.

FIG. 10 is a flowchart illustrating the operation of supplying a transmission clock to the transmission beam former 11B in the third embodiment.

The transmission beam former 11B determines whether a transmission synchronization signal is received from the control circuit 16 (ST31). The transmission beam former 11B stands by until it receives a transmission synchronization signal from the control circuit 16 (NO in ST31).

Having received a transmission synchronization signal from the control circuit 16 (YES in ST31), the clock generator 111 supplies a delay calculation clock to all the delay calculators 112 (ST32). When supplied with the delay calculation clock, each of the delay calculators 112 calculates a delay to be added to a transmission pulse (ST33).

The delay calculated is supplied to each of the pulse generators 113 together with a pulse generation trigger. The pulse generation trigger is also supplied to the clock generator 111. The clock generator 111 determines whether the pulse generation trigger has been received from the delay calculator 112 (ST34).

When the pulse generation trigger has not been received from the delay calculator 112 (NO in ST34), the delay calculator 112 is still performing the transmission delay process. Thus, the clock generator 111 stands by. On the other hand, having received the pulse generation trigger from the delay calculator 112 (YES in ST34), the clock generator 111 stops supplying the delay calculation clock to the delay calculator 112 that has sent the pulse generation trigger (ST35).

At the same time, the clock generator 111 supplies a pulse generation clock to the pulse generator 113 that has received the pulse generation trigger from the delay calculator 112 that has sent the pulse generation trigger (ST36). When supplied with the pulse generation clock from the clock generator 111 and the delayed pulse generation trigger from the delay calculator 112, the pulse generator 113 generates a transmission pulse (ST37).

Then, the pulse generator 113 transmits the transmission pulse generated to the transmitting circuit 12 (ST38). At the same time, the pulse generator 113 sends the clock generator 111 a transmission completion signal of the transmission pulse to the transmitting circuit 12.

The clock generator 111 determines whether the transmission completion signal has been received from the pulse generator 113 (ST39). When the transmission completion signal has not been received from the pulse generator 113 (NO in ST39), the pulse generator 113 is still performing the pulse generation process. Thus, the clock generator 111 stands by.

On the other hand, having received the transmission completion signal from the pulse generator 113 (YES in ST39), the clock generator 111 stops supplying the pulse generation clock to the pulse generator 113 that has sent the transmission completion signal of the transmission pulse (ST40). The time taken for the delay calculators 112 to calculate a delay is the same. However, since the delay added varies, the delay calculators 112 send a delayed pulse generation trigger to the pulse generators 113 at different timings. Accordingly, the transmission completion signal is sent to the clock generator 111 at different times depending on the pulse generators 113. Thus, the clock generator 111 stops the supply of the pulse generation clock sequentially from the pulse generator 113 from which the transmission completion signal has been received.

As described above, according to this embodiment, the clock generator supplies a transmission clock to the delay calculator only in the transmission period, and stops the supply of the clock during the substantial reception period of echo signals, differently from conventional technologies in which the transmission clock is supplied regardless of the transmission period and the reception period. With this, the power consumption in the ultrasound diagnosis apparatus can be reduced. Thus, it is possible to achieve various effects such as the miniaturization of constituent equipment, the integration of channels, and the reduction of noise due to the fluctuation of the power supply voltage. As a result, the ultrasound diagnosis apparatus can be downsized.

Further, in the generation of the transmission pulse, the transmission clock is supplied with respect to the delay calculator of each channel and each pulse generator. In addition, the supply of the delay calculation clock to the delay calculator of each channel or the supply of the pulse generation clock to the pulse generator is stopped under individual control. With this process, the supply of the transmission clock to the delay calculator and the pulse generator can be stopped even during the transmission period. Thus, the power consumption can be further reduced.

Fourth Embodiment

Next, a fourth embodiment will be described. In the fourth embodiment, like reference numerals designate the same constituent elements as those described in the first to third embodiments, and the same description will not be repeated.

In the first to third embodiments so far, the supply of clocks to the delay calculators or the pulse generators in the transmission beam former is appropriately stopped, thereby reducing the power consumption. In the fourth embodiment, the supply of power to the delay calculators and the pulse generators is cut instead of stopping the supply of clocks to reduce the power consumption.

[Configuration of Transmission Beam Former]

Figure 11:
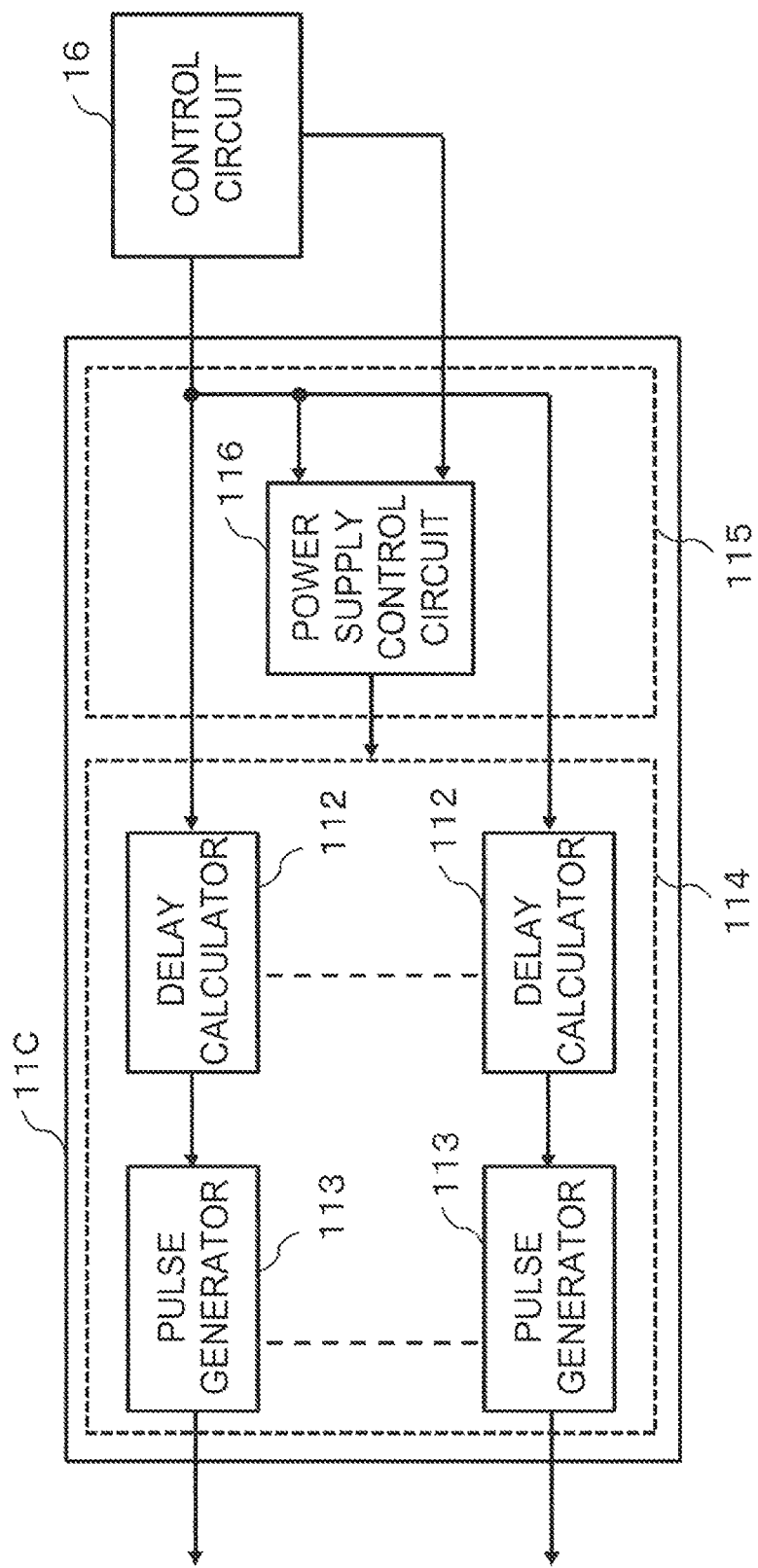
FIG. 11 is a block diagram illustrating a configuration of a transmission beam former according to a fourth embodiment.

FIG. 11 is a block diagram illustrating a configuration of a transmission beam former 11C according to the fourth embodiment. The transmission beam former 11C is connected to the control circuit 16 and is provided with the delay calculators 112 and the pulse generators 113 as in the previous embodiments.

The transmission beam former 11C further includes an ON/OFF control power supply 114 and an always-ON power supply 115. The ON/OFF control power supply 114 supplies power to the delay calculators 112 and the pulse generators 113. On the other hand, the always-ON power supply 115 supplies power to each unit of the transmission beam former 11C except the delay calculators 112 and the pulse generators 113. The transmission beam former 11C further includes a power supply control circuit 116 configured to perform the ON/OFF control of the ON/OFF control power supply 114.

[Operation of Transmission Beam Former and Signal Flow]

The control circuit 16 sends a transmission synchronization signal to the transmission beam former 11C. Having received the transmission synchronization signal, the transmission beam former 11C generates a transmission pulse to be sent to the transmitting circuit 12. For the generation of the transmission pulse, as described above, the delay calculator 112 calculates a delay, and the pulse generator 113 generates the transmission pulse by adding the delay thereto.

The control circuit 16 also sends a transmission/reception determination signal to the power supply control circuit 116. The transmission/reception determination signal is a signal for determining whether ultrasound waves are transmitted from the ultrasound probe 2 to the subject or reflected waves are received as a result of the transmission of ultrasound waves.

In the configuration of the transmission beam former 11C illustrated in FIG. 11, the power supply control circuit 116 controls the ON or OFF of the ON/OFF control power supply 114 based on the transmission/reception determination signal received from the control circuit 16.

Specifically, during the transmission period, the transmission/reception determination signal from the control circuit 16 indicates "transmission". Thus, the power supply control circuit 116 determines that the transmission/reception determination signal indicates "transmission", and controls the ON/OFF control power supply 114 to be turned ON. With this control of the power supply control circuit 116, power is supplied to the delay calculator 112 and the pulse generator 113, and a transmission pulse is generated.

On the other hand, during the substantial reception period, in which reflected waves are received, after the transmission of ultrasound waves to the subject, the transmission/reception determination signal from the control circuit 16 indicates "reception". Accordingly, the power supply control circuit 116 determines that the transmission/reception determination signal indicates "reception", and controls the ON/OFF control power supply 114 to be turned OFF. With this control of the power supply control circuit 116, the supply of power to the delay calculator 112 and the pulse generator 113 is stopped.

In this manner, the power supply control circuit 116 controls the ON/OFF control power supply 114 to be turned OFF during the reception period of reflected waves. Thereby, in this embodiment, power is appropriately supplied to the delay calculator 112 and the pulse generator 113 during the transmission period, while the power supply to the delay calculator 112 and the pulse generator 113 is stopped during the substantial reception period of echo signals. This enables the reduction of power consumption in the ultrasound diagnosis apparatus. Thus, it is possible to achieve various effects such as the miniaturization of constituent equipment, the integration of channels, and the reduction of noise due to the fluctuation of the power supply voltage. As a result, the ultrasound diagnosis apparatus can be downsized.

Next, a modification of the fourth embodiment will be described. The ON/OFF control power supply 114 described above supplies power to all the delay calculators 112 and the pulse generators 113 provided in the transmission beam former 11C. On the other hand, in the modification described below, the power supply to the delay calculators 112 and the pulse generators 113 is performed by a channel power supply 117 provided to each channel.

[Internal Configuration of Transmission Beam Former]

FIG. 12 is a block diagram illustrating another internal configuration of the transmission beam former 11C according to the fourth embodiment. A transmission beam former 11D of the modification has basically the same configuration as that of the transmission beam former 11C except that the channel power supply 117 is provided for each channel. The channel power supply 117 is configured to supply power only to the delay calculator 112 and the pulse generator 113 in each channel. Therefore, power can be supplied and cut off with respect to each channel, that is, for each of the delay calculator 112 and the pulse generator 113 constituting the channel.

[Operation of Transmission Beam Former and Signal Flow]

In this modification, the power supply control circuit 116 receives channel use information from the control circuit 16 in addition to the transmission/reception determination signal. The channel use information is information on a channel being used during the transmission period.

Upon receipt of the channel use information from the control circuit 16 during the transmission period, the power supply control circuit 116 determines whether each channel is in use, that is, ultrasound waves are being transmitted to the subject from the channel, based on the channel use information.

As a result, the channel power supply 117 in a channel being used is controlled to be turned ON. On the other hand, the channel power supply 117 in an unused channel or a channel in which a transmission pulse has already been transmitted to the transmitting circuit 12 is controlled to be turned OFF.

In this manner, the power supply control circuit 116 determines whether a channel is being used or not based on the channel use information to perform the ON/OFF control of the channel power supply 117. Thereby, power is appropriately supplied to the delay calculator 112 and the pulse generator 113 during the transmission period with respect to each channel. Meanwhile, the supply of power to the delay calculator 112 and the pulse generator 113 is stopped during the substantial reception period of echo signals. With this, the power consumption in the ultrasound diagnosis apparatus can be reduced. Thus, it is possible to achieve various effects such as the miniaturization of constituent equipment, the integration of channels, and the reduction of noise due to the fluctuation of the power supply voltage. As a result, the ultrasound diagnosis apparatus can be downsized.

Fifth Embodiment

Next, a fifth embodiment will be described. In the fifth embodiment, like reference numerals designate the same constituent elements as those described in the first to fourth embodiments, and the same description will not be repeated.

In the above embodiments, an ultrasound diagnosis apparatus is cited as an example. In the fifth embodiment, an example will be described in which the transmission beam former of the embodiment is provided to an ultrasound probe P.

[Configuration of Ultrasound Probe]

FIG. 13 is a block diagram illustrating a configuration of the ultrasound probe P according to the fifth embodiment. In the fifth embodiment, the transmission beam former is provided inside the ultrasound probe P as described above. The ultrasound probe P is detachably connected to the ultrasound diagnosis apparatus.

The ultrasound probe P includes a transmission beam former 31 configured to generate a transmission pulse, a transmitting circuit 33 configured to supply a drive signal to ultrasound transducers 32, a receiving circuit 34 configured to receive a reflection signal from the ultrasound probe P, a reception beam former 35 configured to process the reflection signal, and a control circuit 36 configured to control each unit.

Note that, while the internal configuration of the ultrasound probe P of the fifth embodiment has been described above, it is only the configuration supposed to be necessary for explaining the fifth embodiment. Therefore, the ultrasound probe P may further include a configuration not illustrated in FIG. 5.

Under the control of the control circuit 36, the transmission beam former 31 generates a transmission pulse, which is a drive signal to be transmitted from the transmitting circuit 33 and applied to the ultrasound transducers 32. The transmission beam former 31 calculates a delay corresponding to the distance between each of the ultrasound transducers 32 and a focal point such that the phases of ultrasound waves transmitted from the ultrasound transducers 32 to the subject are aligned at a predetermined focal point in the subject and generates a transmission pulse (drive signal) to which the delay is added.

The transmission beam former 31 includes a clock generator 311, a delay calculator 312, and a pulse generator 313. The clock generator 311 receives a transmission synchronization signal and a transmission clock from the control circuit 36, and generates a clock to be supplied to the delay calculator 312 and the pulse generator 313. The delay calculator 312 calculates a delay to be added to each transmission pulse. The pulse generator 313 generates a transmission pulse to be supplied to the transmitting circuit 33. The transmission pulse supplied from the pulse generator 313 to the transmitting circuit 33 is applied to the ultrasound transducers 32 as a drive signal.

FIG. 13 illustrates one clock generator (311) in the transmission beam former 31. A combination of the delay calculator 312 and the pulse generator 313 is provided with respect to each channel. There are a plurality of channels, and a plurality of the delay calculators 312 and the pulse generators 313 are provided in the transmission beam former 31. However, in FIG. 13, only two pairs of the delay calculator 312 and the pulse generator 313 are illustrated, and others are not illustrated.

The ultrasound probe P transmits and receives ultrasound waves in a state where its distal end surface is in contact with the surface of the subject. The ultrasound probe P incorporates a plurality of the ultrasound transducers 32, which are one-dimensionally arranged on the distal end surface. The ultrasound probe P transmits ultrasound waves to the inside of the subject by each of the ultrasound transducers 32 to scan the scan area, and receives reflected waves from the subject as echo signals. Examples of the scan include various scans such as B mode scan and Doppler mode scan.

In addition, examples of the ultrasound probe P include a sector scan probe, a linear scan probe, a convex scan probe, and the like. Any of these probes is arbitrarily selected according to an area to be diagnosed. The ultrasound transducers 32 need not necessarily be arranged one-dimensionally. If the ultrasound transducers 32 are arranged two-dimensionally, volume data can be acquired in real time. In the case of obtaining a three-dimensional stereoscopic image, a three-dimensional scanning probe is used as the ultrasound probe P. A two-dimensional array probe or a mechanical four-dimensional probe can be cited as an example of the three-dimensional scanning probe.

FIG. 13 does not illustrate all of the ultrasound transducers 32 built in the ultrasound probe P. FIG. 13 illustrate only two ultrasound transducers (32), and the illustration of others is omitted by a broken line provided between the two ultrasound transducers 32.

The transmitting circuit 33 receives the transmission pulse generated by the transmission beam former 31, and transmits it to the ultrasound transducers 32 as a drive signal. As a configuration of the transmitting circuit 33, for example, the configuration of a switch pulser or a linear driver can be employed.

The receiving circuit 34 receives a reflection signal (echo signal) from the ultrasound transducers 32. The echo signal received by the receiving circuit 34 is fed to the reception beam former 35. The reception beam former 35 adds a delay to the echo signal, and outputs the signal acquired by the delay addition to the scan converter of the ultrasound diagnosis apparatus to which the ultrasound probe P is connected.

[Operation of Transmission Beam Former and Signal Flow]

Next, a description will be given of the operation of the transmission beam former and a signal flow. As described above, the transmission beam former 31 generates a transmission pulse (drive signal) to be applied to the ultrasound transducers 32. First, the clock generator 311 is fed with a transmission synchronization signal and a transmission clock from the control circuit 36. Not only the clock generator 311 but also the delay calculator 312 of each channel is fed with the transmission synchronization signal from the control circuit 36.

The clock generator 311 supplies the transmission clock to each of the delay calculators 312 and the pulse generators 313 when the ultrasound probe P enters a period for transmitting ultrasound waves (transmission waves) to the subject therefrom. The clock generator 311 supplies the transmission clock concurrently to all the delay calculators 312 in the transmission beam former 31.

Upon receipt of the transmission clock from the clock generator 311, each of the delay calculators 312 calculates a delay to be added to a transmission pulse. The delay calculator 312 supplies a pulse generation trigger including the delay to the pulse generator 313 connected thereto.

The pulse generator 313 generates a transmission pulse to be supplied to the transmitting circuit 33 by adding thereto the delay received from the delay calculator 312. As described above, the transmission pulse generated is applied to the ultrasound transducers 32 through the transmitting circuit 33.

The ultrasound probe P alternately performs the transmission of ultrasound waves to the subject and the receipt of reflected waves. Accordingly, a transmission period for transmitting ultrasound waves and a reception period for receiving reflected waves are alternately provided. The transmission pulse generated by the transmission beam former 31 is applied to the ultrasound transducers 32 during the transmission period. When the transmission period is switched to the reception period, the application of the transmission pulse to the ultrasound transducers 32 is terminated.

Having transmitted the transmission pulse generated to the transmitting circuit 33, the pulse generator 313 transmits a transmission completion signal to the clock generator 311. In FIG. 13, an arrow extending from the pulse generator 313 to the clock generator 311 represents the transmission completion signal transmitted from the pulse generator 313 to the clock generator 311. Upon receipt of the transmission completion signal transmitted from all the pulse generators 313, the clock generator 311 stops the supply of the transmission clock to the delay calculators 312 and the pulse generator 313.

In FIG. 13, an arrow extending from the clock generator 311 toward the left in the figure indicates that the transmission clock is supplied to all the delay calculators and the pulse generators concurrently, and also the supply of the transmission clock is stopped concurrently for all the delay calculators and the pulse generators.

As described above, according to this embodiment, the clock generator supplies a transmission clock to the delay calculator only in the transmission period, and stops the supply of the clock during the substantial reception period of echo signals, differently from conventional technologies in which the clock generator supplies a transmission clock to the delay calculator regardless of the transmission period and the reception period. With this, the power consumption in the ultrasound probe can be reduced. Thus, it is possible to achieve various effects such as the miniaturization of constituent equipment, the integration of channels, and the reduction of noise due to the fluctuation of the power supply voltage. As a result, the ultrasound diagnosis apparatus can be downsized.

An example has been described in which the ultrasound probe is provided with a transmission beam former configured to stop the supply of transmission clocks to the delay calculators during the reception period, thereby reducing the power consumption (the first embodiment). The transmission beam former mounted on the ultrasound probe may be configured to, for example, control the supply of the transmission clock and the stop thereof with respect to each channel (the second embodiment). Further, the transmission beam former may be configured to control the supply of the clock and the stop thereof with respect to each delay calculator and each pulse generator (the third embodiment), or control the supply of power and the stop thereof instead of the clock (fourth embodiment) for reducing the power consumption.

In the above embodiments, the clock generator supplies various clocks and stops the supply of the clocks. In addition, the power supply control circuit controls the supply of power in the transmission beam former. However, for example, the control circuit may perform these control operations.

Although several embodiments have been described regarding the supply of various clocks and the stop thereof or the supply of power and the stop thereof in the transmission beam former, the features of the embodiments may be combined to form further embodiments. As a result, the power consumption can be further reduced.

While certain embodiments have been described, these embodiments have been presented by way of example only, and are not intended to limit the scope of the inventions. Indeed, the novel embodiments described herein may be embodied in a variety of other forms; further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
a transmission beam former configured to generate a transmission pulse; and
a plurality of transmitting circuits configured to supply a plurality of ultrasound transducers with transmission pulses received from the transmission beam former, wherein
supply of a clock necessary for generation of the transmission pulses is stopped during a reception period of echo signals from the plurality of ultrasound transducers,
the transmission beam former includes:
a plurality of pulse generators configured to generate the transmission pulses to be supplied to the plurality of transmitting circuits;
a plurality of delay calculators configured to calculate a plurality of delays to be added to the transmission pulses, respectively; and
a clock generator configured to generate the clock to be supplied to the plurality of delay calculators and the plurality of pulse generators, and
the clock generator is further configured to:
being triggered by reception of transmission completion signals from all the plurality of pulse generators, stop the supply of the clock to the plurality of delay calculators during the reception period of echo signals from the plurality of ultrasound transducers; and
cause the plurality of delay calculators to wait for operation until the clock generator receives a transmission synchronization signal.

2. The ultrasound diagnosis apparatus of claim 1, wherein the clock is supplied or the supply of the clock is stopped with respect to each channel of the plurality of transmitting circuits.

3. The ultrasound diagnosis apparatus of claim 2, wherein the clock is supplied or the supply of the clock is stopped with respect to each of the plurality of delay calculators or each of the plurality of pulse generators respectively constituting a channel.

4. The ultrasound diagnosis apparatus of claim 2, wherein the clock is supplied to a channel used in an examination mode selected for an examination to be performed on a subject.

5. The ultrasound diagnosis apparatus of claim 3, wherein the clock is supplied to a channel used in an examination mode selected for an examination to be performed on a subject.

6. The ultrasound diagnosis apparatus of claim 2, wherein the clock is supplied to a channel used in an ultrasound probe connected to the ultrasound diagnosis apparatus.

7. The ultrasound diagnosis apparatus of claim 3, wherein the clock is supplied to a channel used in an ultrasound probe connected to the ultrasound diagnosis apparatus.

8. The ultrasound diagnosis apparatus of claim 1, wherein the clock generator is further configured to:
being triggered by the reception of the transmission completion signals from all the plurality of pulse generators, stop the supply of the clock to the plurality of delay calculators and the plurality of pulse generators during the reception period of echo signals from the plurality of ultrasound transducers; and
cause the plurality of delay calculators and the plurality of pulse generators to wait for operation until the clock generator receives the transmission synchronization signal.

9. An ultrasound probe, comprising:
a transmission beam former configured to generate a transmission pulse; and
a plurality of transmitting circuits configured to supply a plurality of ultrasound transducers with transmission pulses received from the transmission beam former, wherein
supply of a clock necessary for generation of the transmission pulses is stopped during a reception period of echo signals from the plurality of ultrasound transducers,
the transmission beam former includes:
a plurality of pulse generators configured to generate the transmission pulses to be supplied to the plurality of transmitting circuits;
a plurality of delay calculators configured to calculate a plurality of delays to be added to the transmission pulses, respectively; and
a clock generator configured to generate the clock to be supplied to the plurality of delay calculators and the plurality of pulse generators, and
the clock generator is further configured to:
being triggered by reception of transmission completion signals from all the plurality of pulse generators, stop the supply of the clock to the plurality of delay calculators during the reception period of echo signals from the plurality of ultrasound transducers; and
cause the plurality of delay calculators to wait for operation until the clock generator receives a transmission synchronization signal.

10. The ultrasound probe of claim 9, wherein the clock is supplied or the supply of the clock is stopped with respect to each channel of the plurality of transmitting circuits.

11. The ultrasound probe of claim 10, wherein the clock is supplied or the supply of the clock is stopped with respect to each of the plurality of delay calculators respectively constituting a channel.

12. The ultrasound probe of claim 10, wherein the clock is supplied to a channel used in an examination mode selected for an examination to be performed on a subject.

13. The ultrasound probe of claim 11, wherein the clock is supplied to a channel used in an examination mode selected for an examination to be performed on a subject.

* * * * *